US00PP32963P3

(12) United States Plant Patent
Beckman

(10) Patent No.: US PP32,963 P3
(45) Date of Patent: Apr. 6, 2021

(54) CALLA LILY PLANT NAMED 'PETER'S PRIDE'

(50) Latin Name: *Zantedeschia sprengeri*
Varietal Denomination: Peter's Pride

(71) Applicant: Dümmen Group B.V., De Lier (NL)

(72) Inventor: Peter Beckman, Santa Cruz, CA (US)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 16/602,423

(22) Filed: Oct. 1, 2019

(65) Prior Publication Data

US 2020/0113107 P1 Apr. 9, 2020

Related U.S. Application Data

(60) Provisional application No. 62/766,205, filed on Oct. 4, 2018.

(51) Int. Cl.

| | |
|---|---|
| ***A01H 6/10*** | (2018.01) |
| ***A01H 5/02*** | (2018.01) |
| ***A01H 6/56*** | (2018.01) |

(52) U.S. Cl.

USPC ..... Plt./490
CPC ..... *A01H 6/56* (2018.05)

(58) Field of Classification Search

USPC ..... Plt./490
CPC ..... A01H 6/10; A01H 5/02
See application file for complete search history.

*Primary Examiner* — Keith O. Robinson
(74) *Attorney, Agent, or Firm* — The Webb Law Firm

(57) ABSTRACT

'Peter's Pride' is a new variety of calla lily plant having hot pink colored spathes. The leaves are green with maculations present.

1 Drawing Sheet

Botanical classification: *Zantedeschia sprengeri.*
Varietal denomination: 'Peter's Pride'.

BACKGROUND OF THE NEW PLANT

The present invention comprises a new and distinct cultivar of calla lily, botanically known as *Zantedeschia sprengeri* and hereinafter referred to by the cultivar name 'Peter's Pride'.

'Peter's Pride' is a product of a planned breeding program having the objective of creating *Zantedeschia* varieties for pot flower production in a wide range of colors and classic flower shapes. 'Peter's Pride' was selected in 2006 in Moss Landing, Calif. as an inbred seedling selected from an open-pollinated population and self-pollinated for many generations. As such, its exact parentage is unknown and comparisons thereto cannot be provided.

The new variety was first asexually reproduced through tissue culture shoot propagation in October of 2006 in Moss Landing, Calif. Asexual reproductions of 'Peter's Pride' have demonstrated that the combination of characteristics as herein disclosed for the new variety are retained and reproduced true to type through successive generations of asexual reproduction.

The following observations, measurements and comparisons describe plants grown in 15 cm pots at 84 days from planting in 't Zand, The Netherlands under greenhouse conditions which approximate those generally used in horticultural practice. Color references are made to The 2001 R.H.S. Colour Chart of The Royal Horticultural Society of London, 4$^{th}$ Edition, except where general color terms of ordinary significance are used.

The present invention has not been evaluated under all possible environmental conditions. The phenotype may vary with variations in environment without a change in the genotype of the plant.

The following traits have been repeatedly observed and determined to be basic characteristics of 'Peter's Pride' which, in combination, distinguish this calla lily as a new and distinct cultivar:

1. Hot pink colored spathes; and
2. Leaf maculations present.

Table 1 provides a comparison of 'Peter's Pride' to similar *Zantedeschia sprengeri* varieties 'Twilight' (unpatented), 'Garnet Glow' (unpatented), and 'Flirt' (unpatented). Further, the new variety flowers seven days earlier than 'Garnet Glow'.

TABLE 1

| Comparison variety | Differing trait(s) | Comparison expression | Present variety expression |
|---|---|---|---|
| 'Twilight' | Spath color | Lavender | Hot pink (Red Group RHS 55B) |
| 'Garnet Glow' | Leaf Maculations | None present | Present |
| 'Flirt' | Spathe color | Reddish pink | Hot pink (Red Group RHS 55B) |

BRIEF DESCRIPTION OF THE DRAWING

The accompanying photographic drawing illustrates the new variety at 84 days from planting, with the colors being as nearly true as is possible with color illustrations of this type.

DESCRIPTION OF THE NEW PLANT

Type: Deciduous.
Form: Semi-spreading.
Average spread: 43-60 cm.
Branch number: High.

Branch color: Yellow-Green Group RHS 145A to 145B.
Height of leaf canopy above the soil: 21-25 cm.
Height of top of inflorescences above the soil.—27-33 cm.
Number of inflorescences per tuber.—>20 cm in diameter: 17-32.
Lastingness of inflorescences on the plant: About 14 days.
Main use: Potted plant.
Average time of flowering: Tubers planted in the field in May in 't Zand, The Netherlands bloom in July. Tubers planted in a greenhouse in February in 't Zand, The Netherlands bloom in April.
Disease/pest resistance: Moderate to good tolerance to Pythium root rot and Erwinia bulb soft rot.
Hardiness: Not tested.
Leaves:
*Number per plant.*—52-68.
*Width.*—4-5 cm, with broadest position in the middle.
*Length.*—21-25.5 cm.
*Shape.*—Lanceolate.
*Apex.*—Apiculate.
*Base.*—Attenuate.
*Margin.*—Entire.
*Color.*—Upper surface: Green Group RHS 137B to 137C, with Green-White Group RHS 157A to 157B maculations present. Lower surface: Green Group RHS 143B to 143C, with White Group RHS 155A to 155B maculations present.
*Surface texture.*—Smooth (both surfaces).
*Leaf venation.*—Pattern: Pinnate. Color: Yellow-Green Group RHS 145A to 145B.
*Lobes.*—None present.
*Petiole.*—Length: 23-25 cm. Diameter: 10-13 mm. Texture: Smooth. Shape: Cylindrical. Strength: Medium to strong. Color: Upper surface: Yellow-Green Group RHS N144C to N144D. Lower surface: Yellow-Green Group RHS 144C to 144D.
Spathe:
*Length.*—4.5-5 cm.
*Width.*—3-4.5 cm.
*Fragrance.*—None.
*Shape.*—Leaf-like.
*Texture.*—Smooth.
*Apex.*—Caudate.
*Base.*—Amplexicaul.
*Margin.*—Entire.
*Color.*—Throat spot: Purple-Violet Group RHS N82B. Upper surface: Red-Purple Group RHS 73A to 73B. Lower surface: Red-Purple Group RHS N74B to N74C.
Spadix:
*Length.*—25-33 mm.
*Diameter.*—4-9 mm.
*Color.*—Yellow Group RHS 6B to 6C.
*Position relative to spathe.*—Upright from base.
*Apex.*—Rounded and Yellow Group RHS 6B to 6C.
*Pollen amount.*—Abundant.
Peduncle:
*Length.*—27-34 cm.
*Diameter.*—8-11 mm.
*Texture.*—Smooth.
*Color.*—Base: Yellow-Green Group RHS 145B to 145C. Upper portion: Yellow-Green Group RHS 144B to 144C.
Seeds:
*Number/flower.*—27.
*Length.*—3.5-4.5 mm.
*Diameter.*—2.1-3.8 mm.
*Color.*—White Group RHS 155C.
Reproductive organs:
*Anther.*—Shape: Round. Length: Less than 1 mm. Color: Yellow Group RHS 8B to 8C.
*Filament.*—Length: Less than 1 mm. Color: White Group RHS 155D.
*Style.*—Length: Less than 1 mm. Color: Yellow Group RHS 8B to 8C.
*Pistil.*—Number: 15-30. Length: About 1 mm.
*Stigma.*—Shape: Round. Length: Less than 1 mm. Diameter: Less than 1 mm.
*Ovaries.*—Texture: Smooth. Length: Varies between 1 to 10 mm. Diameter: Varies between 1 to 10 mm. Color: Top: Yellow-Orange Group RHS 16C to 16D. Bottom: Yellow Group RHS 2C to 2D.

I claim:

1. A new and distinct variety of calla lily plant named 'Peter's Pride' as herein described and illustrated.

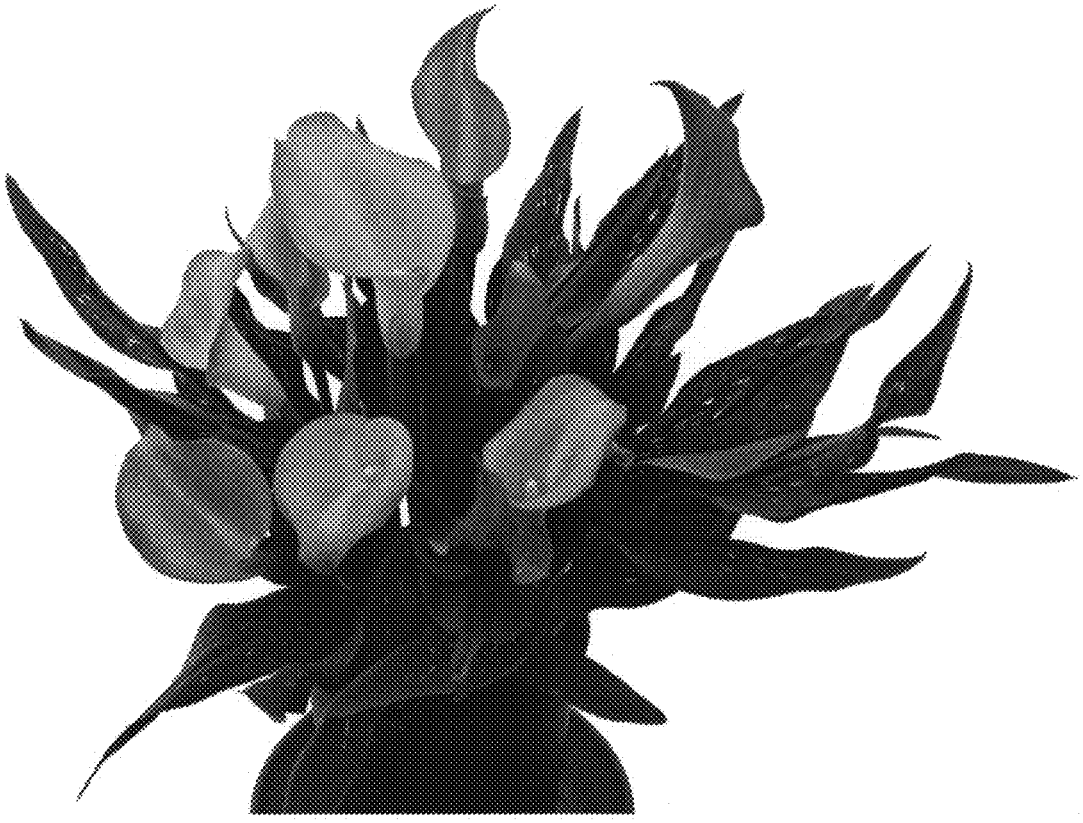

* * * * *